United States Patent [19]

Spano et al.

[11] Patent Number: 5,342,401
[45] Date of Patent: Aug. 30, 1994

[54] REAL TIME CARDIAC ARRHYTHMIA STABILIZING SYSTEM

[75] Inventors: Mark L. Spano, Laurel, Md.; William L. Ditto, Wooster, Ohio; Alan Garfinkel, Venice; James N. Weiss, Encino, both of Calif.

[73] Assignee: The Regents of the University of California, Oakland, Calif.

[21] Appl. No.: 930,945

[22] Filed: Aug. 19, 1992

[51] Int. Cl.⁵ ............................................. A61N 1/00
[52] U.S. Cl. .......................................... 607/5; 607/9; 607/17
[58] Field of Search ............ 128/419 D, 419 PG, 702; 364/413.05, 413.06; 607/5, 9, 17

[56] References Cited

U.S. PATENT DOCUMENTS

| | | | |
|---|---|---|---|
| 4,732,157 | 3/1988 | Kaplan et al. | 128/702 X |
| 4,827,932 | 5/1989 | Ideker et al. | 607/5 |
| 5,109,842 | 5/1992 | Adinolfi | 607/5 |
| 5,201,321 | 4/1993 | Fulton | 128/702 |

OTHER PUBLICATIONS

Gulick, *Encounters with Chaos*, 1992, pp. 159–161.
Glass et al., *From Clocks to Chaos*, 1988, pp. 160–167.
Gleick, *Chaos, Making a New Science*, 1987, pp. 280–292.

Primary Examiner—Lee S. Cohen
Assistant Examiner—Jeffrey R. Jastrzab
Attorney, Agent, or Firm—Jacob Shuster

[57] ABSTRACT

Electrical stimuli delivered to cardiac tissue at times determined from a chaos stabilizing algorithm, converts arrhythmia activity to periodic beating by an interbeat interval shortening action, utilizing real time calculation based on a system parameter experimentally determined from intervention by the electrical stimuli.

9 Claims, 5 Drawing Sheets

REAL TIME CARDIAC ARRHYTHMIA STABILIZING SYSTEM

BACKGROUND OF THE INVENTION

This invention relates in general to monitoring, analyzing and modifying the pulsating behavior of active systems, and in particular that of living cardiac tissue.

The realization that many activities of an apparently random nature are actually examples of a deterministic phenomenon known as chaos offers a new approach to analysis and modification of complex systems. Phenomena that have been shown to exhibit chaos include the transition to turbulence in fluids, many mechanical vibrations, irregular oscillations in chemical reactions, the rise and fall of epidemics and the irregular dripping of a faucet. Several studies have argued that certain cardiac arrhythmias are also examples of an irregular pulsating behavior characterizable as chaos.

Until recently the main strategy for dealing with a system exhibiting chaos was to develop a model of the system sufficiently detailed to identify the key parameters and then to change those parameters enough to take the system out of the chaotic regime. However that strategy is limited to systems for which a theoretical model is known and which do not display irreversible parametric changes (often the very changes causing the chaos) such as aging. Recently, a strategy was developed which does not attempt to take the system out of the chaotic regime but uses the chaos to control the system, The critical feature of chaos believed to make this possible is the extreme sensitivity of chaotic systems to perturbations of their initial conditions. The key to such strategy lies in the fact that chaotic motion includes an infinite number of unstable periodic motions. A chaotic system never remains long in any of such unstable motions but continually switches from one periodic motion to another, thereby giving the appearance of randomness. It was conjectured that it should be possible to stabilize a chaotic system around selected periodic motions. Such system stabilizing theory and approach was first applied experimentally (a) to controlling the chaotic vibrations of a magnetoelastic ribbon and (b) subsequently applied to a diode resonator circuit and (c) in the chaotic output of lasers. Such chaos controlling strategy involved development of a realtime measurement of the current system state and identification of an unstable fixed point of interest on a plot along with its stable and unstable manifolds. Such fixed point and its accompanying manifolds shift in response to changes in system-wide parameters. Thus, a feedback providing algorithm was developed tending to move the fixed point and manifolds toward the system state point on the aforementioned plot in response to corrective control of the selected system-wide parameter. Unfortunately, a system-wide parameter capable of being changed with sufficient rapidity to implement corrective control in accordance with the foregoing strategy was not found to be suitable in certain cases for stabilization purposes.

It is therefore an important object of the present invention to provide a method and apparatus for manipulating chaotic behavior based on the aforementioned study of chaotic regimes by intervention at irregular times determined from real time calculations involving data obtained by monitoring a selected observable system behavior.

SUMMARY OF THE INVENTION

In accordance with the present invention, a procedure for stabilization of living tissue pulsations involves monitoring the timing of intervals between pulsation beats and experimental determination of interbeat intervals in response to a single stimulus intervention pulse. Interbeat interval monitoring is performed during a learning phase typically lasting approximately 5 to 60 seconds in order to determine by real time calculation the approximate locations of the unstable fixed point of a chaotic regime at the intersection of its stable and unstable directions (manifolds) plotted as a function of the observable interbeat interval change. When the learning phase is completed, an intervention waiting period is instituted based on the close approach of interbeat interval timing to the unstable fixed point, such intervention being based on switching of the chaotic regime to a periodic condition according to natural system behavior. Thus at the end of such waiting period, intervention by premature injection of a stimulus pulse causes a shift to an interbeat interval system state point as a variable, lying on the stable manifold path from which it monotonically approaches the unstable fixed point, by exclusive increase or decrease of such variable. An important aspect of the present invention therefore involves real time measurement and exploitation of the aforesaid natural behavior without any theoretical model.

The aforementioned intervention waiting period is terminated by said premature injection of the stimulus pulse causing advance of the interbeat interval and movement of the system state point onto the stable manifold toward the unstable fixed point. If the next spontaneous pulse beat corresponds to an .interbeat interval point close to the unstable fixed point, the intervention phase is terminated and the behavior stabilization program is recycled. Otherwise, another intervention stimulus pulse is injected before recycling.

The foregoing behavior stabilization program of monitoring interbeat intervals, performing real time calculations and delaying premature injection of stimulus pulses, if applied by way of example to the control system of a cardiac pacemaker should restore or resume periodic frequency beat control activity. Such a behavior stabilization program is based on the recognition that the chaotic regime of cardiac tissue is characterized by natural motion of interbeat interval points along unstable paths toward or away from the unstable fixed point and such chaos is controllable by a properly delayed intervention of injected stimulus pulses tending to shorten the interbeat interval.

BRIEF DESCRIPTION OF DRAWING FIGURES

Other objects, advantages and novel features of the invention will become apparent from the following detailed description of the invention when considered in conjunction with the accompanying drawing wherein.

DETAILED DESCRIPTION OF PREFERRED EMBODIMENT

In accordance with one embodiment of the invention, living tissue preparation in the form of an isolated well-perfused portion of the interventricular septum from a rabbit heart was arterially perfused through a septal branch of its coronary artery with a physiologic oxygenated Kreb's solution at 37° C. The tissue was stimulated by injection of 3 m constant voltage pulse into a Grass SD9 stimulator connected to platinum electrodes in contact with the preparation and triggered by computer control. Electrical activity was monitored to record monophasic action potentials through Ag—AgCl wires on the surface of the tissue. Monophasic action potentials and a stimulus marker tracing were recorded on a modified videocassette recorder (Model 420, A. R. Vetter, Inc.) and one of the monophasic action potential traces was simultaneously digitized at 2 kHz by a 12-bit A-D converter board (National Instruments Model AT-MO-16). The digitized trace was processed on-line by a 486 computer to detect the activation time of each beat from the maximum of the first derivative of the voltage signal.

Figure 1A:
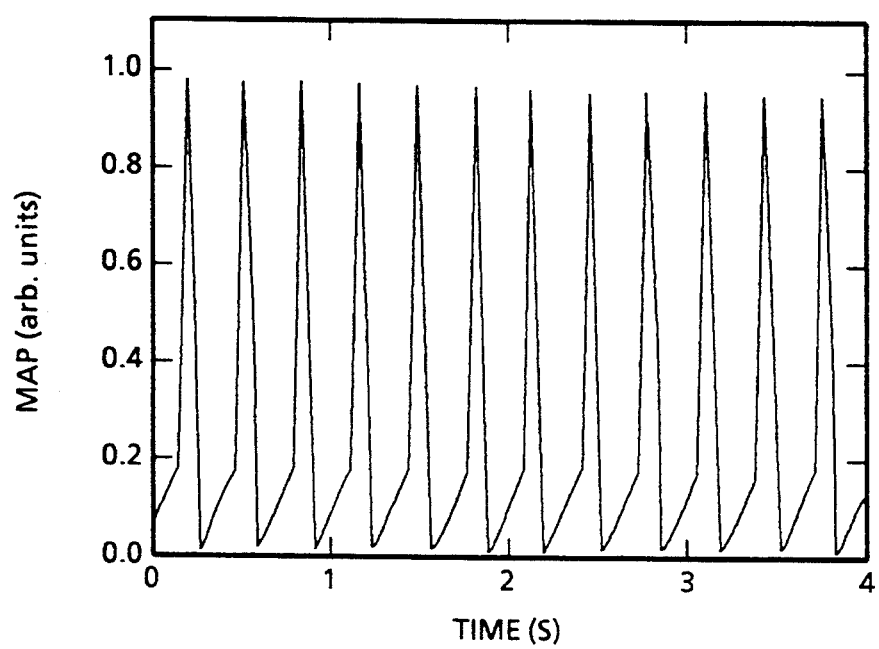
FIGS. 1A, 1B, 1C and 1D are graphical plots of monophasic action potentials characterizing spontaneous periodic beating of cardiac tissue at a constant interbeat interval (1A), higher order periodicities (1B, 1C) and chaotic (1D) patterns.
Figure 1B:
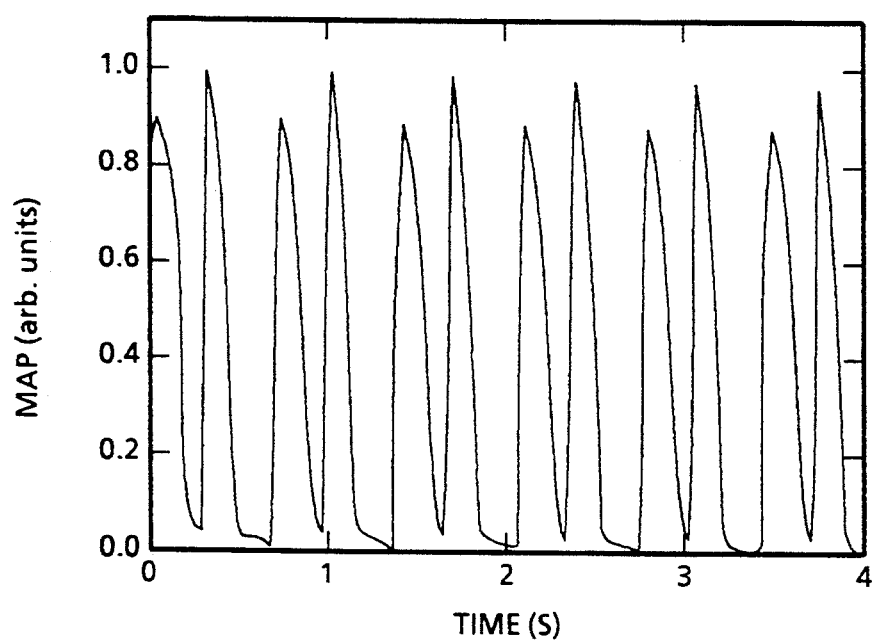
Figure 1:
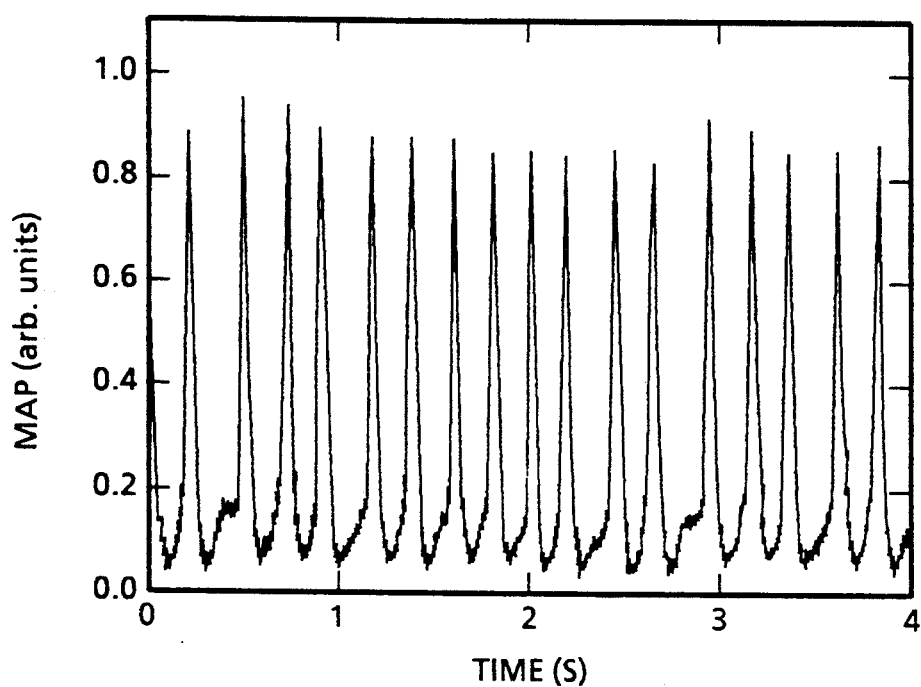
Figure 1C:
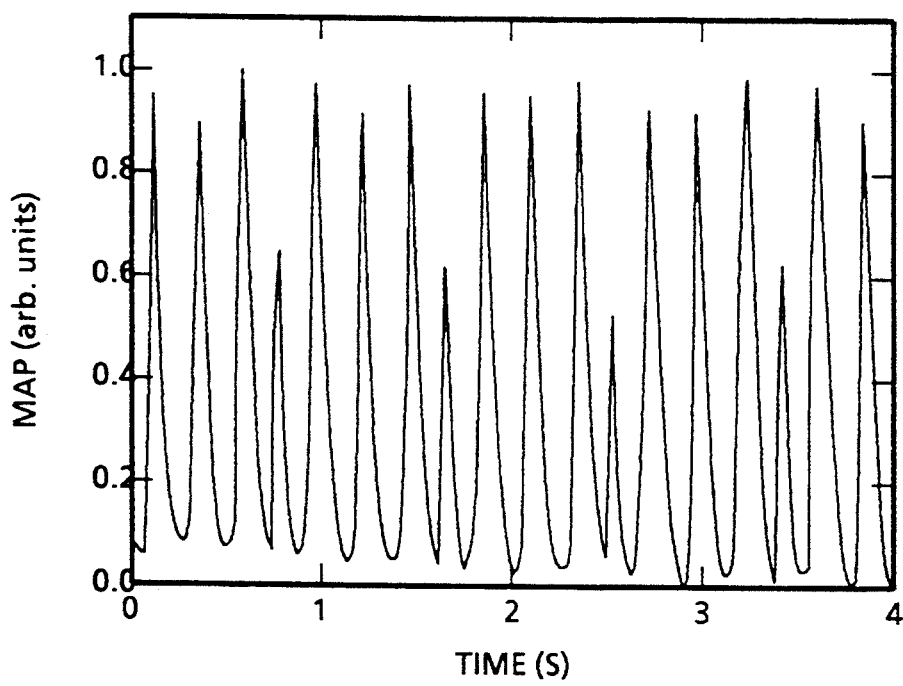

Arrhythmias were induced in the tissue by adding 2–5 $\mu M$ ouabain with or without 2–10 $\mu M$ epinephrine to the arterial perfusate. The mechanism of ouabain-/epinephrine-induced arrhythmias is probably a combination of triggered activity and non-triggered automaticity caused by progressive intracellular $Ca^{2+}$ overload from $Na^+$ pump inhibition and increased $Ca^{2+}$ current. The resultant oscillations in intracellular $Ca^{2+}$ caused spontaneous beating by activating arrhythmogenic inward currents from electrogenic $Na^+$-$Ca^{2+}$ exchange and $Ca^{2+}$ activated nonselective cation channels. Typically the ouabain/ephinephrine combination induced spontaneous beating, initially at a constant interbeat interval as graphically plotted in FIG. 1A, then progressing to bigeminy and high order periodicity, as depicted in FIGS. 1B and 1C, before development of a highly irregular aperiodic pattern of spontaneous activity in 85% of the preparations as shown in FIG. 1D. The duration of the aperiodic phase was variable, lasting up to several minutes before electrical activity ceased, probably corresponding to progressive severe membrane depolarization from $Na^+$pump inhibition. The spontaneous activity so induced showed a number of features symptomatic of chaos. Most importantly, in progressing from spontaneous beating at a fixed interbeat interval to highly aperiodic behavior, the arrhythmia passed through a series of transient stages that involved higher order periodicities. The arrhythmia then progressed to an aperiodic stage characteristic of a chaotic rather than a random process.

Figure 2:
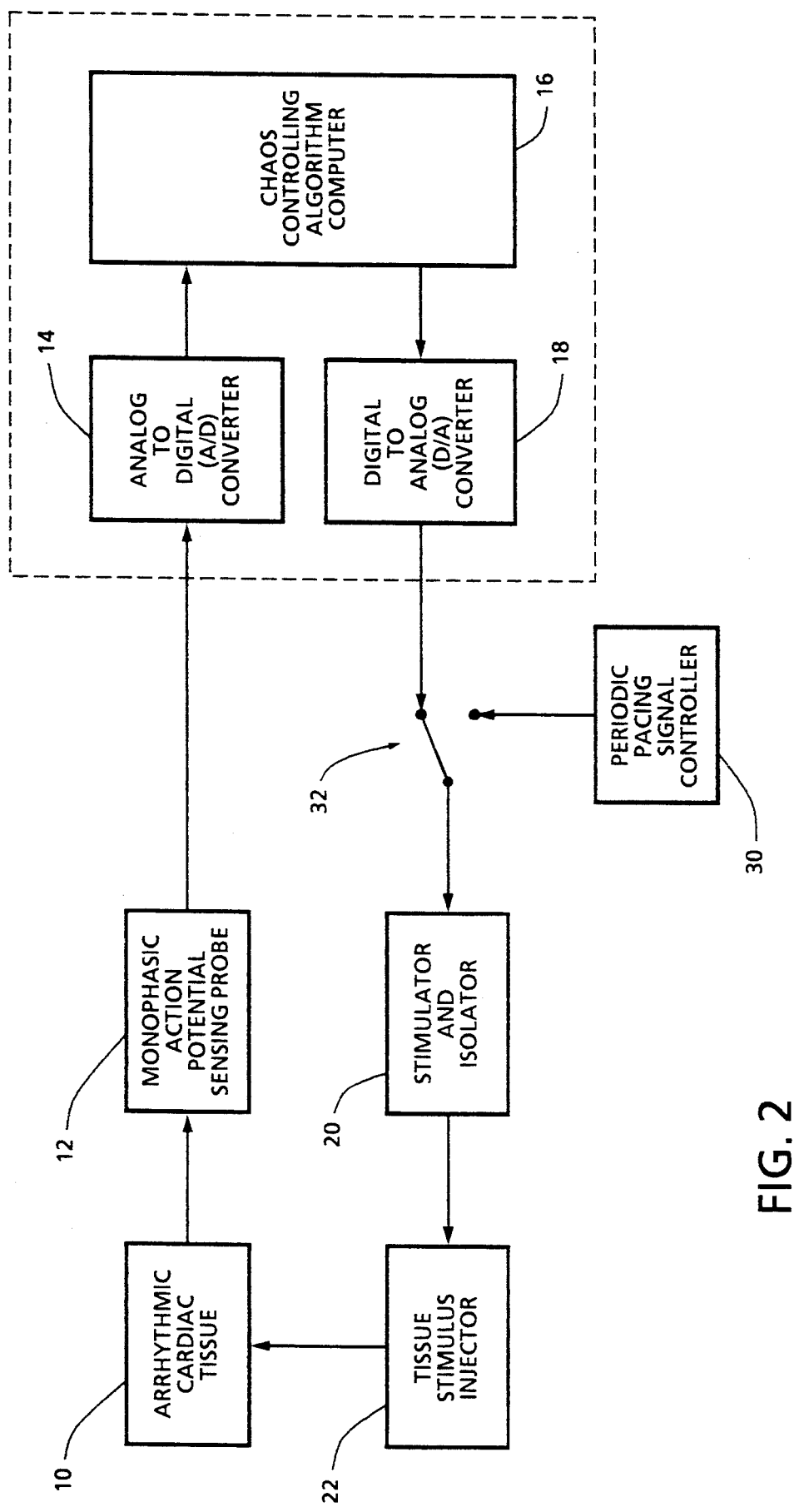
FIG. 2 is a block diagram illustrating a chaos controlling system in accordance with one embodiment of the invention.

FIG. 2 diagrams a typical hardware arrangement associated with the foregoing embodiment of the invention, wherein tissue 10 hereinbefore described and arterially perfused, exhibited a pulsating behavioral activity. The concomitant electrical signal was detected by a monophasic action potential (MAP) type sensor 12 for digitization through an analog-to-digital converter 14. The output data of the converter 14 was fed to a chaos behavior controlling computer 16 as diagrammed in FIG. 2. Chaos control by computer 16 was effected under a software program for monotonic intervention involving delivery of a stimulus pulse into tissue 10 after a spontaneous pulse beat by means of a digital-to-analog converter 18 actuating a tissue stimulator and isolator 20 to energize a stimulus injector 22. Consequently, the intervening stimulus injection through injector 22 required the computer 16 to predict the timing of the next beat in order to anticipate and shorten the interbeat interval.

Figure 3:
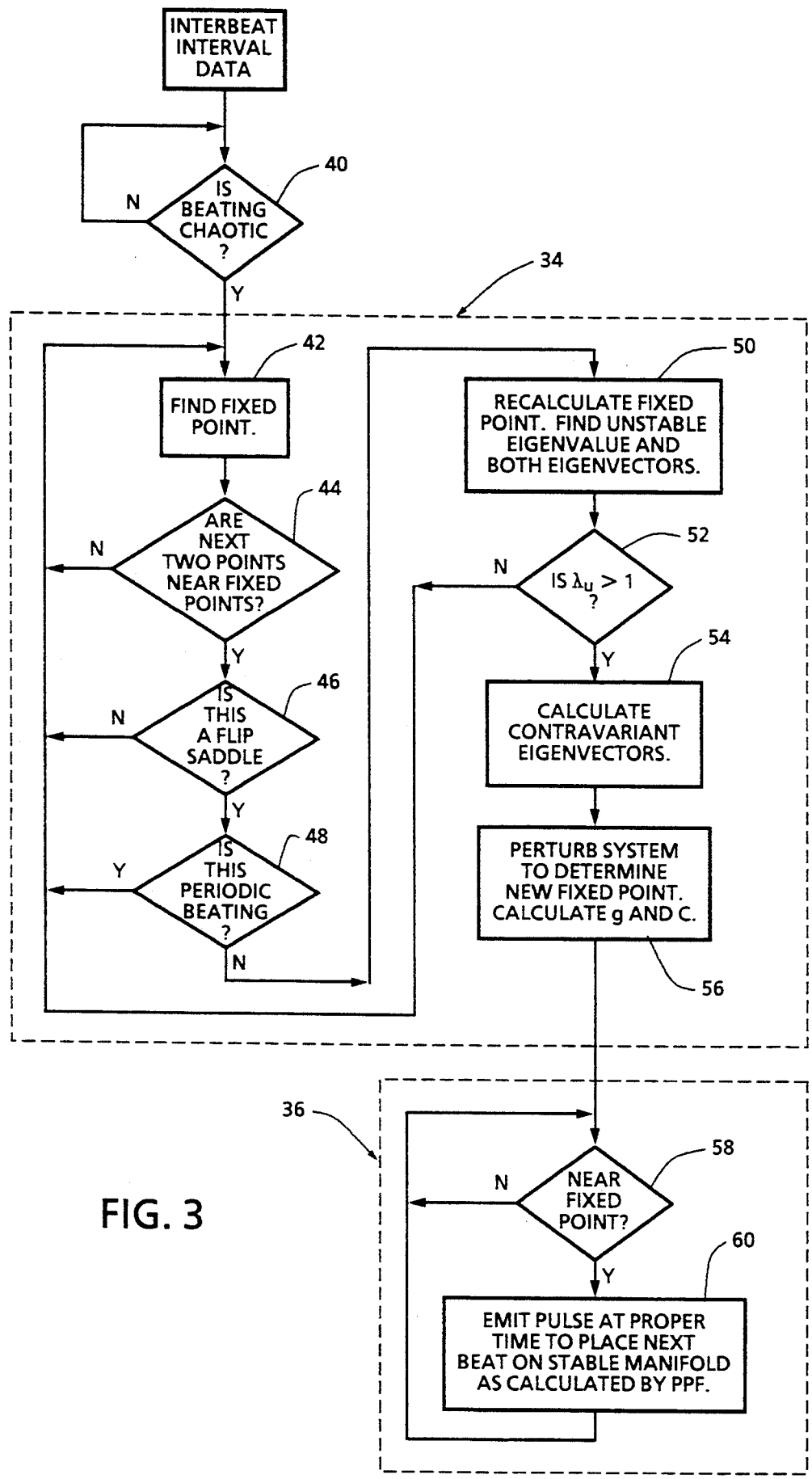
FIG. 3 is a flow chart diagram of the software program associated with the computer diagrammed in FIG. 2.

Injection of the intervening stimulus by the hardware arrangement as diagrammed in FIG. 2, is under control of the computer software program as diagrammed in FIG. 3. The tissue stimulator 20 may alternatively be actuated by a fixed periodic beat controller 30, such as a cardiac pacemaker, that is disabled by a chaos control switch 32 as also diagrammed in FIG. 2.

The software program of computer 16 consists of a learning phase section 34 and a control phase section 36 as diagrammed in .FIG. 3. Entry of measurement input data from probe 12 through converter 14 to computer 16 initiates the learning phase for real time calculation in accordance with the computer algorithm. Thus, interbeat interval data from converter 14 is repeatedly monitored in the computer 16 pursuant to step 40 of the software program until chaotic beating occurs. The interval data is then plotted pursuant to program step 42 to initiate the learning phase 34. Plotting of the intervals between chaotic beats involved use of delay indicating coordinates of current interbeat interval $(I_n)$ vs. previous interbeat interval $(I_{n-1})$ to determine first an unstable fixed point. When such fixed point is so determined by program step 42, two following system state points on the delay coordinate plot are examined during program step 44 to see if they are local or close to the fixed point within a radial distance $\epsilon$, within which distance the local geometry is approximately linear. If such two points are local, the geometry is examined pursuant to program step 46 to ensure that it is a flip saddle. The points are then examined during the next program step 48 to re-verify that the beats are not periodic. If any of the tests performed during the program steps 44, 46 and 48 fails, the learning phase is restarted as diagrammed in FIG. 3. When all such tests are passed, the fixed point is recalculated during program step 50 to determine the local eigenvectors and the unstable eigenvalue as components of the local geometry. The magnitude of the eigenvalue $(\lambda_u)$ is then tested during program step 52 to determine if it is larger than unity. If not, beating is not chaotic and the learning phase is restarted as denoted in FIG. 3. If $\lambda_u > 1$, the program continues to the calculation step 54 for determination of the contravariant eigenvectors. The final step 56 of the learning phase involves system perturbation to observe the resulting change in fixed point location. Such observation enables calculation of the quantities (g) and (C) hereinafter referred to and terminates the learning phase.

The control phase 36 is initiated upon termination of the learning phase 34, as diagrammed in FIG. 3, by program step 58 determining approach to the fixed point on the delay coordinate plot aforementioned. If the approach is close (within radial distance $\epsilon$), the next calculation step 60 is triggered, whereby a stimulus pulse is inserted and another pulse emitted at the proper time for continued monitoring of interbeat intervals and to await another close approach to the fixed point.

Figure 4:
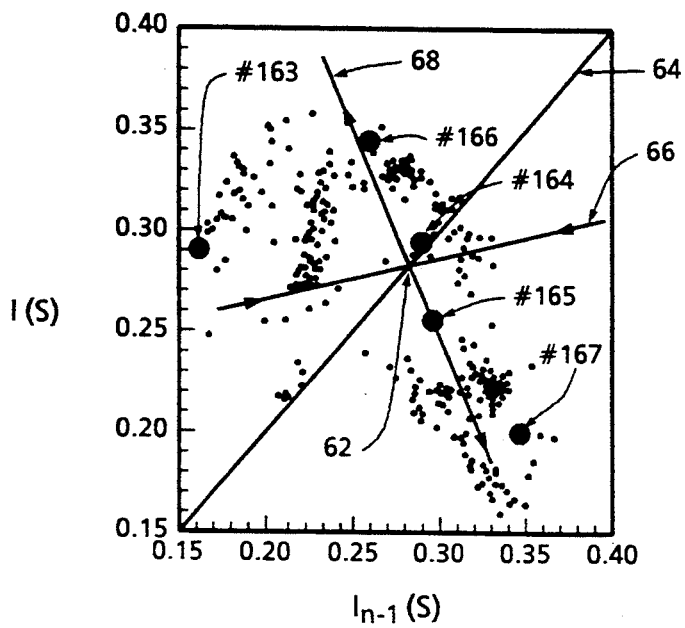
FIG. 4 is a graphical interbeat interval plot or Poincare map of the aperiodic phase of the induced arrhythmia of animal cardiac tissue to which the present invention was applied.

As hereinbefore described, the aperiodic behavior or arrhythmia induced in the tissue 10 involved transient high order periodicities, as graphically depicted in FIG. 4 wherein the nth interbeat interval ($I_n$) has been plotted against the previous interval ($I_{n-1}$) at various stages. A typical sequence of interbeat intervals during induced aperiodic beating is depicted wherein a shift in the state of the system from point 163 to 164 occurs toward an unstable fixed point 62 lying on the line of identity 64. Thus point 163 lies close to stable manifold 66. Points 164 through 167 on the other hand diverge from the unstable fixed point 62 and hence reveal an unstable manifold 68. The local geometry around fixed point 62 in the plot of FIG. 4 is that of a saddle. In this case the saddle is a flip saddle as aforementioned in connection with program step 46 in FIG. 3; that is, while the distances of successive state points 163-167 from the fixed point 62 monotonically increase in an exponential fashion along the unstable manifold 68 (one of the signs of chaos) the state points alternate on opposite sides of the stable manifold 66. The flip saddle is manifested by a short interbeat interval followed by a long interval and vice versa.

In accordance with the present invention, perturbation of the system being monitored is effected when the state point monotonically approaches the unstable fixed point 62, such perturbation forcing the system state point onto the stable manifold 66 as depicted, for example, in FIG. 4. As a result, the system state point will naturally move toward the unstable fixed point 62 rather than away from it, in sharp contrast to prior art methods wherein the stable manifold 66 would instead be moved toward the current system state point. Pursuant to such prior art methods, as well as in the present invention, a linear approximation of the dynamics in the neighborhood of the desired unstable fixed point 62 is utilized. According to prior art theory however, a system-wide parameter must be varied to move the stable manifold 66 toward the system state point, whereas movement of the system state point toward the stable manifold 66 by proportional perturbation feedback (PPF) is effected pursuant to the present invention without parameter change. Such proportional perturbation feedback (PPF) method is particularly useful where the cardiac tissue preparation possesses no systemwide parameter that can be changed with sufficient rapidity to implement corrective control.

The aforementioned proportional perturbation feedback procedure begins by determining the location $\vec{\xi}_F$ of the unstable fixed point 62 as hereinbefore denoted by step 42 in FIG. 3, as well as its local stable and unstable manifolds 66 and 68. From such determinations, the stable and unstable contravariant eigenvectors $\vec{f}_s$ and $\vec{f}_u$ are derived as denoted by step 50 in FIG. 3. If $\vec{\xi}_n$ is the location of the current system state point on the Poincare map of FIG. 4, and p is the predicted timing of the next natural beat as the system parameter, the required advance in timing $\delta p$ is proportional to the projection of the distance $\vec{\xi}_n - \vec{\xi}_F$ onto the unstable manifold 68, expressed as:

$$\delta p = C(\vec{\xi}_n - \vec{\xi}_F)\vec{u} \qquad (1),$$

where:

$$C = \frac{\lambda_u}{\lambda_u - 1} \frac{1}{\vec{g} \cdot \vec{f}_u}. \qquad (2)$$

Thus, the constant of proportionality C depends on the unstable eigenvalue $\lambda_u$, which determines the rate of the exponential divergence of the system from the fixed point 62 along the unstable manifold 68. The eigenvalue $\lambda_u$ is readily determined from the sequence of system state points 164 through 167 as denoted in FIG. 4. The term $\vec{g}$ relates to the sensitivity of points near the fixed point 62 to the advance in timing $\delta p$, and is approximated as:

$$\vec{g} = \frac{\partial \vec{\xi}_F}{\partial p}.$$

The constant C is thus inversely proportional to the projection of $\vec{g}$ onto the unstable manifold. The system perturbation $\delta p$ represents the amount of time to shorten an anticipated natural beat (by introducting a stimulus) to force the state point onto the stable manifold 66. The foregoing proportional feedback control procedure is performed during the aforementioned learning and intervention phases 34 and 36.

During the learning phase 34, the interbeat interval is monitored until the approximate locations of the unstable fixed point 62 and the stable and unstable manifolds 66 and 68 are determined pursuant to the program diagrammed in FIG. 3. The application of equations (1) and (2) during the intervention control phase 36 would then be straightforward once the geometry of the local plot around the fixed point 62 has been determined and the quantity $\vec{g}$ has been found. However the tissue 10 lacks an obvious system-wide parameter that could be changed rapidly enough to implement classical control. Accordingly, the interbeat interval, while not a system-wide parameter, is directly manipulated by shortening it with an electrically stimulated pulse pursuant to the present invention. Therefore, the timing of the next interbeat interval is chosen as the analogue of the system parameter p. The sensitivity of the state point to changes in p was determined experimentally by noting the change in the interbeat interval in response to a single stimulus pulse when the state point was near the fixed point. Thus, pursuant to methods heretofore based on the local geometry about an unstable fixed point, wherein electrically stimulated pulses move the stable manifold toward the state point of the system, the state point itself is moved toward the stable maniford of the system in accordance with the present invention by the intervening stimuli.

Figure 5A:
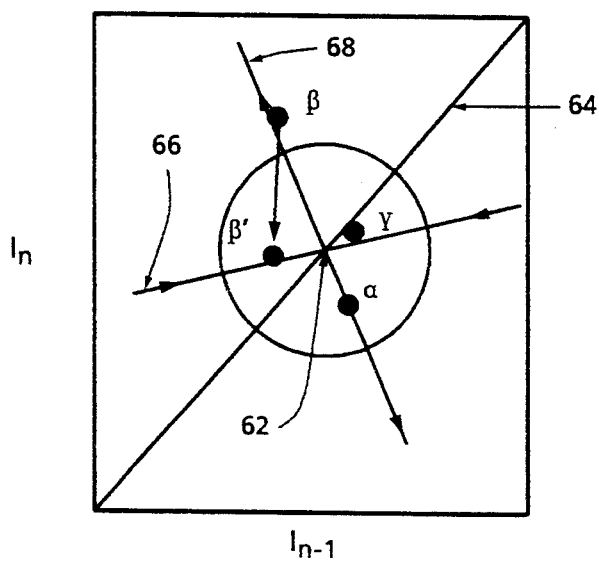
FIGS. 5A and 5B are exemplary interbeat interval plots corresponding to FIG. 4, depicting a chaos controlling sequence.
Figure 5B:
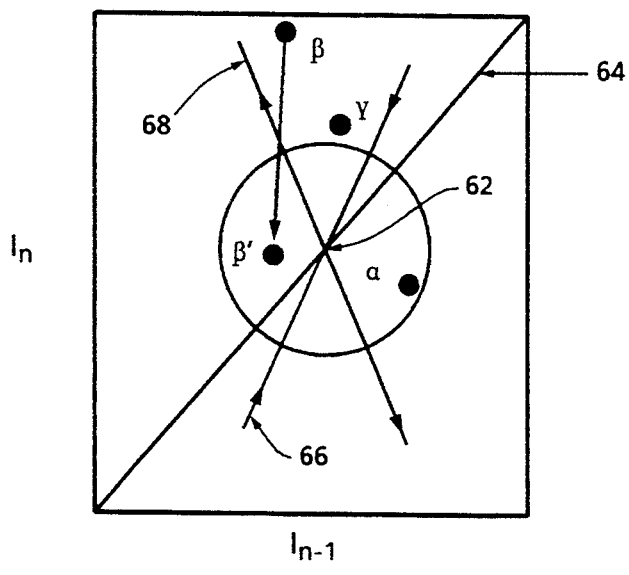

The learning phase 34 typically lasts from 5 to 60 seconds, after which the chaos controlling algorithm of computer 16 waits for the system to make a close approach to the unstable fixed point at a system state point $\alpha$, as depicted in FIG. 5A within circle 70 of radius $\epsilon$. The next point would normally fall further out along the unstable manifold (as well as on the opposite side of the stable manifold), as indicated by point $\beta$. However at this point the computer 16 intervenes pursuant to its algorithm by injecting the electrical stimulus early enough so that the state point actually occurs at $\beta'$, lying directly below $\beta$ and by construction near the stable manifold 66. Since the system is now close to the stable manifold, ideally the subsequent spontaneous beat would tend to move closer to the fixed point 62 along the stable manifold. Thus, state point γ would be confined to the region near the unstable fixed point 62, thereby regularizing the arrhythmia. However in actual practice this degree of accuracy was not typically obtained. FIG. 5B illustrates the usual result. When point β' does not fall precisely on the stable manifold 66, point γ often is not extremely close to the fixed point 62 (falls outside the circle 70) but still lies fairly close to the stable manifold (since β' was close to the stable manifold). Nevertheless, point γ lies closer to the stable manifold than point α. Thus, the next point falls within the circle 70 in the vicinity of α and restarts the cycle (as a new point α). As the foregoing procedural pattern is repeated, a periodic beating results. In this manner, the chaotic (arrhythmia) beating is made periodic by only intermittent stimuli. The foregoing approach did not require any theoretical model and all quantities required were calculated in real time from the input data.

Using the algorithm hereinbefore set forth, control of the chaotic phase of the induced arrhythmia was successful in most experimental runs performed. When the arrhythmia became chaotic, the chaos control program was activated as hereinbefore indicated. The criteria for detecting chaos is the plot of FIG. 4 exhibiting stable and unstable manifolds with a flip saddle roughly along the linear part of the unstable manifold 68. More specifically, chaos detection involves an observed monotonic shift of the system state point towards the fixed point 62, thereby directionally determining the stable manifold 66, followed by monotonic shift from the fixed point along a clearly different direction corresponding to the unstable manifold 68. The chaos control program then chose and delivered electrical stimuli as previously described. In order to prove that chaos control was achieved and maintained (defined as a clear conversion of a chaotic sequence to a periodic one) the chaos control program was shut down and a return to chaotic behavior was consistently observed sometimes preceded by transient complex periodicities.

Several observations were apparent from the pattern of the stimuli delivered by the chaos control program hereinbefore described. First, the stimuli did not simply overdrive the system. Stimuli were delivered sporadically, not on every beat and never more than once in every three beats on average. The pattern of stimuli was initially erratic and aperiodic, but soon became approximately periodic as the arrhythmia was converted to a nearly periodic rhythm. Thus, the chaos control program rapidly converted the aperiodic behavior of the arrhythmia to a periodic rhythm. In contrast, periodic pacing by controller 30, as depicted in FIG. 2, through which stimuli was heretofore delivered at a fixed rate was never effective in restoring a periodic rhythm and often made the aperiodicity more marked. Other pacings of an irregular type were heretofore similarly ineffective in converting chaotic to periodic behavior.

It is interesting to note that in several cases chaos control in accordance with the present invention had the additional effect of eliminating the shortest interbeat intervals, hence reducing the average rate of tachycardia. Without an understanding of the chaotic nature of the system, it would seem paradoxical that an intervention that could only shorten the interbeat intervals would result in a lengthening of the average interval. However, since very long interbeat intervals tend to be followed by very short interbeat intervals (a consequence of the properties of the flip saddle), elimination of the very long intervals also tends to eliminate very short intervals. In cases in which very short intervals predominate during the arrhythmia, their elimination during chaos control will tend to lengthen the average interbeat interval between spontaneous beats. Thus, where chaos was successfully controlled, the chaotic pattern of the arrhythmia was converted to a low order periodic pattern.

Numerous other modifications and variations of the present invention are possible in light of the foregoing teachings. It is therefore to be understood that within the scope of the appended claims the invention may be practiced otherwise than as specifically described.

What is claimed is:

1. In a method of treating pulsating behavioral activity by monitoring interbeat intervals of said activity to detect a chaos system and intervening to effect a shift in status of the chaos system from movements of system state points along an unstable manifold to movements along a stable manifold, including the steps of: performing real time calculation during said monitoring of the interbeat intervals to determine changes in the status of the chaos system from data obtained by said monitoring of the interbeat intervals; and deriving from said real time calculation a waiting time for delaying said intervening in accordance with a chaos behavior controlling algorithm; said delayed intervening including injecting stimulus pulses causing said shift in the status of the chaos system tending to shorten certain of the interbeat intervals.

2. The method of claim 1 wherein said pulsating behavioral activity is associated with living animal tissue to which the stimulus pulse are applied by said step of injecting.

3. The method of claim 2 wherein said living animal tissue is an interventricular system of a rabbit heat that is arterially perfused, and including the step of inducing cardiac arrhythmia in said heat to produce the pulsating behavioral activity.

4. A method of treating cardiac arrhythmia induced in an arterially perfused interventricular system of a rabbit heart, comprising the steps of: monitoring interbeat intervals of said cardiac arrhythmia to detect a chaos system as movements of system state points along stable and unstable manifolds; performing real time calculation from data obtained by said monitoring of the interbeat intervals to determine changes in status of the chaos system; deriving from said real time calculation a waiting time in accordance with a chaos behavior controlling algorithm: $\delta p = C(\xi_n - \xi_F) \cdot fu$; where γn is a vector position of the interbeat intervals, $\xi_F$ is a position of an unstable fixed point of the interbeat intervals, fu is a contravariant eigenvector associated with the unstable manifold and C is a constant of proportionality; and instituting intervention to effect a shift in status of the chaos system from said movements of the system state points along the unstable manifold to said movements along the stable manifold tending to shorten certain of the interbeat intervals; including the steps of: injecting stimulus pulses into the rabbit heart during said interbeat intervals, delayed by said waiting time, to cause said shift in the status of the chaos system; and experimentally determining a change in a system parameter from change in the interbeat intervals caused by a single one of the stimulus pulses; said constant of proportionality being equal to $$\frac{\lambda u}{\lambda u - 1} \cdot \frac{1}{g \cdot fu},$$

where λu is an unstable eigenvalue and g is a change in the position ($\xi_F$) of the unstable fixed point relative to said change in the system parameter.

5. A method of treating pulsating behavioral activity by intervention, comprising the steps of: monitoring interbeat intervals of said activity during a learning phase; performing real time calculation to detect status changes in a chaotic regime during said learning phase; determining from said real time calculation a waiting period; and instituting said intervention upon termination of the waiting period following the learning phase.

6. A method of controlling pulsating activity of living tissue having spontaneous beats, including the steps of: measuring intervals of said activity; monitoring variation of said measured interbeat intervals to detect establishment of a chaotic regime; generating a stimulus pulse; determining a system parameter of said pulsating activity; determining a waiting period from an algorithm: $C(\xi_n - \xi_F) \cdot fu$; where $\xi_n$ is a vector position of the interbeat intervals, $\xi_F$ is a position of an unstable fixed point of the interbeat intervals, fu is a contravariant eigenvector of the interbeat intervals varying from said fixed point along an unstable manifold and C is a constant of proportionality equal to:

$$\frac{\lambda u}{\lambda u - 1} \cdot \frac{1}{g \cdot fu},$$

where λu is an unstable eigenvalue and g is a change in the position ($\xi_F$) of the unstable fixed point relative to change in said system parameter; and injecting the stimulus pulse into the living tissue delayed by said waiting period following one of the spontaneous beats, whereby the chaotic regime is converted to a substantially constant interbeat interval regime by said injecting of the stimulus pulse.

7. The method of claim 6 including the steps of: arterially perfusing an interventricular system of a heart as the living tissue and inducing cardiac arrhythmia in said heart as the pulsating activity.

8. A method of controlling pulsating activity of living tissue having spontaneous beats, including the steps of: measuring interbeat intervals of said activity; monitoring variation of said measured interbeat intervals to detect establishment of a chaotic regime; generating a stimulus pulse; experimentally determining a parameter of said pulsating activity; performing a real time calculation, based on said parameter, to determine a waiting period following one of said spontaneous beats; and injecting the stimulus pulse into the living tissue upon completion of said waiting period to convert the chaotic regime to a substantially constant interbeat interval regime.

9. The method of claim 8, wherein said real time calculation is performed in accordance with a chaos behavior controlling algorithm.

* * * * *

UNITED STATES PATENT AND TRADEMARK OFFICE
CERTIFICATE OF CORRECTION

PATENT NO. : 5,342,401
DATED : August 30, 1994
INVENTOR(S) : Spano et al.

It is certified that error appears in the above-indentified patent and that said Letters Patent is hereby corrected as shown below:

In Column 1, before "BACKGROUND OF THE INVENTION" the following Government acknowledgment should be inserted: -- This invention was made with Government support under Grant No. HL 44880; Grant No. HL 36729, awarded by the National Institutes of Health. The Government has certain rights in this invention. --

Signed and Sealed this

Twenty-fifth Day of May, 1999

Attest:

Q. TODD DICKINSON

*Attesting Officer*     Acting Commissioner of Patents and Trademarks